Figure 1:
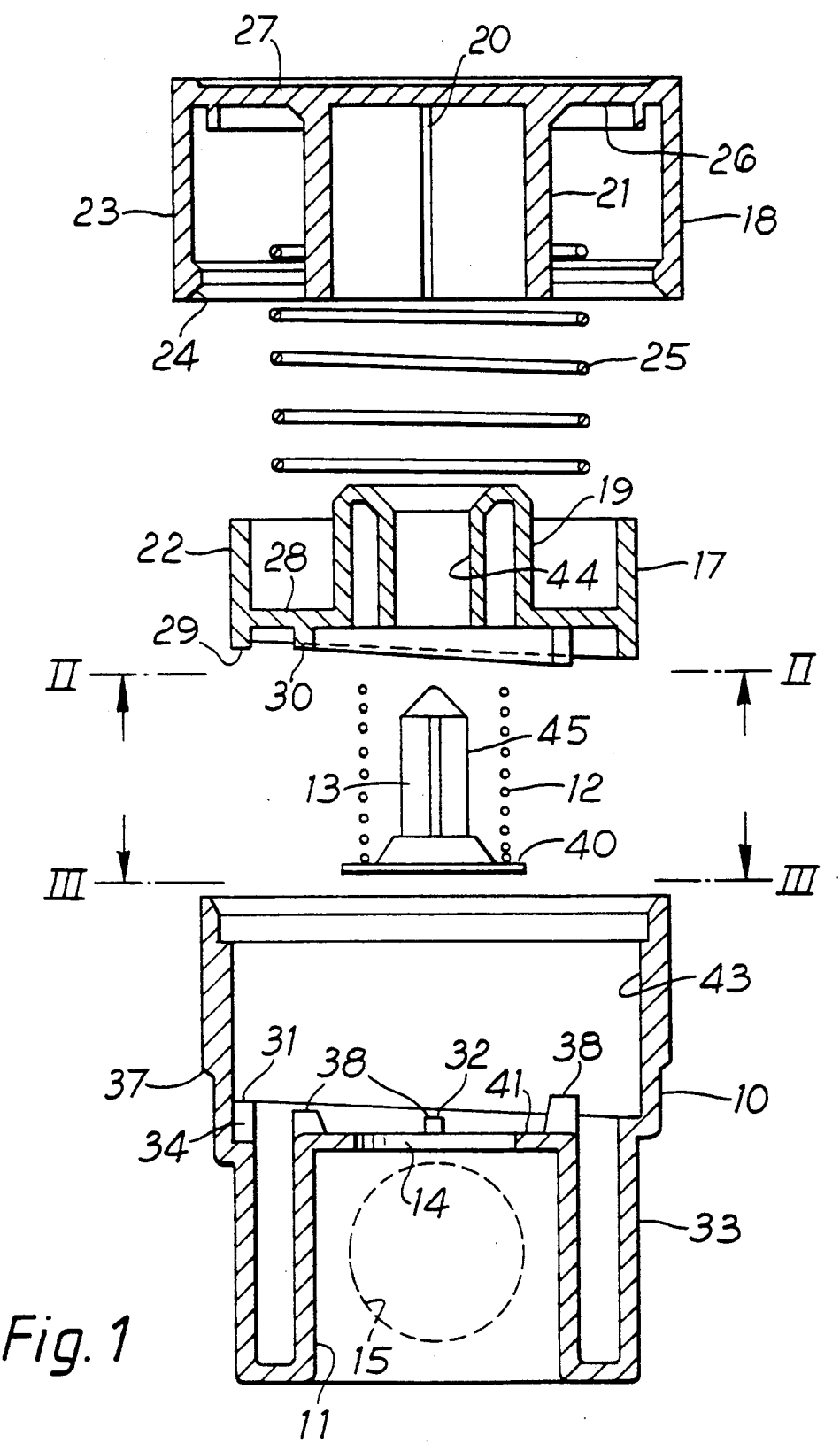

United States Patent [19]

Hicks

[11] Patent Number: 5,141,024
[45] Date of Patent: Aug. 25, 1992

[54] VALVE WITH PAIRED HELICAL RAMPS

[75] Inventor: Richard B. Hicks, Kingston-upon-Thames, United Kingdom

[73] Assignee: Intersurgical Limited, Twickenham, United Kingdom

[21] Appl. No.: 730,877

[22] PCT Filed: Feb. 1, 1990

[86] PCT No.: PCT/GB90/00165
§ 371 Date: Jul. 17, 1991
§ 102(e) Date: Jul. 17, 1991

[87] PCT Pub. No.: WO90/08566
PCT Pub. Date: Aug. 9, 1990

[30] Foreign Application Priority Data

Feb. 1, 1989 [GB] United Kingdom ............... 8902181

[51] Int. Cl.⁵ .......................................... F16K 17/06
[52] U.S. Cl. ................................. 137/530; 137/542; 251/256
[58] Field of Search ............... 137/530, 542; 251/256

[56] References Cited

U.S. PATENT DOCUMENTS 2,521,166 9/1950 Hinrichs ........................... 137/530
4,762,145 8/1988 Stradella ....................... 137/530 X Primary Examiner—Robert G. Nilson
Attorney, Agent, or Firm—Young & Thompson

[57] ABSTRACT

Axial displacement between two components of a valve occurs as a result of relative rotation through the cooperation of helical ramps. Preferably another pair of helical ramps is provided concentric with the first but angularly offset 180° with the result that when the components are at maxinum axial separation the residual contact between the ramps of each pair (shaded areas in FIG. 5e) will be on opposite sides of the axis x of rotation and prolongation, thus preventing tilting of the one component out of axial alignment with the other component. In other constructions more than two pairs of ramps are employed. The ramp means of the invention replaces a screw-thread to provide adjustment of the loading of a valve spring and permits the use of more economical manufacturing and assembly techniques.

5 Claims, 4 Drawing Sheets

VALVE WITH PAIRED HELICAL RAMPS

This invention relates to a valve, by which is meant any device, such as a tap, which is adapted to control the flow of a fluid (gas or liquid) through a supply or discharge line therefor.

The commonest examples of valves currently available employ a screw-thread, which additionally interconnects the components of the valve and is often used solely for this purpose.

There are applications, however, where it is not necessary or where it is actually undesirable that there should be a screw-threaded connection. In mass production the provision of a screw-thread is relatively expensive. It cannot be made by the simplest moulding operation involving the removal of a (fixed) die from a mould because the opposed sides of the screw-thread in the mould would prevent this. A collapsing or rotating die has to be used to produce a screw thread in a plastics material. Alternatively if the screw thread is provided in metal components it is produced by precision cutting. In addition to being relatively expensive to manufacture a screw-threaded device does not lend itself to automated assembly techniques because the components must be precisely aligned and relatively rotated.

One object of the present invention is to provide a valve which is more economical to manufacture and to assemble than one employing a screw thread.

In accordance with the present invention there is provided a valve comprising a tubular housing having a valve seat therein, a valve member control element having a generally cylindrical periphery which is a sliding and rotational fit within the tube, a cap covering the end of the tubular housing remote from the valve seat, said cap engaging the housing so as to be manually rotatable but not axially displaceable relative thereto and means being provided interengaging the cap and the control element whereby the control element is axially displaceable but non-rotatable relative to the cap, the housing and the control element being provided with a plurality of concentric pairs of opposed helical ramp means of different diameters, the ramp means of each pair being of similar diameter and opposed to one another axially of the housing and oppositely arranged whereby sliding contact between the ramp means as the control element is rotated will cause axial displacement of the latter toward or away from the valve seat, adjacent pairs being angularly offset about the axis of the housing, a compression spring means being entrapped between the cap and the control element to bias the latter toward the valve seat and the two ramp means of each pair being of similar, constant pitch and are configured to provide sliding contact between continuous surfaces, or between a continuous and a discontinuous surface of the ramp means of each pair when the control element and housing are relatively rotated.

Said pairs of ramp means may be two in number and may be angularly offset 180°.

Alternatively opposed faces of the housing and of the control element may be provided each with more than two helical ramp means of differing diameter, each said ramp means of one component being paired with a similar ramp means of the other component and each pair of ramp means being angularly offset with respect to the or each adjacent pair according to the formula:

$$\text{optimum offset} = \frac{360°}{\text{No. of concentric helical ramps.}}$$

The control element may have an axial bore in which a stem of a valve member is axially slidable, the valve member having a head at one end of the stem between which head and the control element a compression spring is located to bias the head of the valve member into contact with the valve seat, the arrangement being such that axial displacement of the control element within the housing adjusts the pressure of the spring loading under which the head of the valve member is held on the valve seat.

Any one of said ramp means of each pair thereof may be discontinuous, being constituted by angularly separated abutments the surfaces of which presented to the other ramp means of the pair all lie on a helix of pitch and diameter similar to those of said other ramp means.

Figure 2:
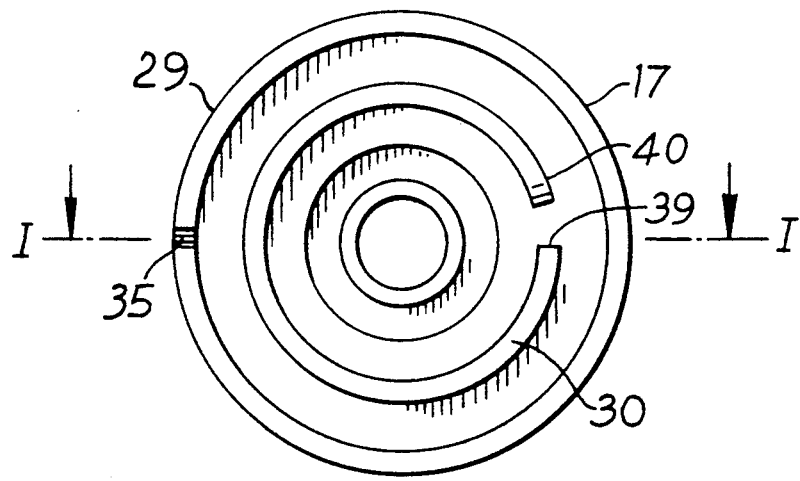
Figure 3:
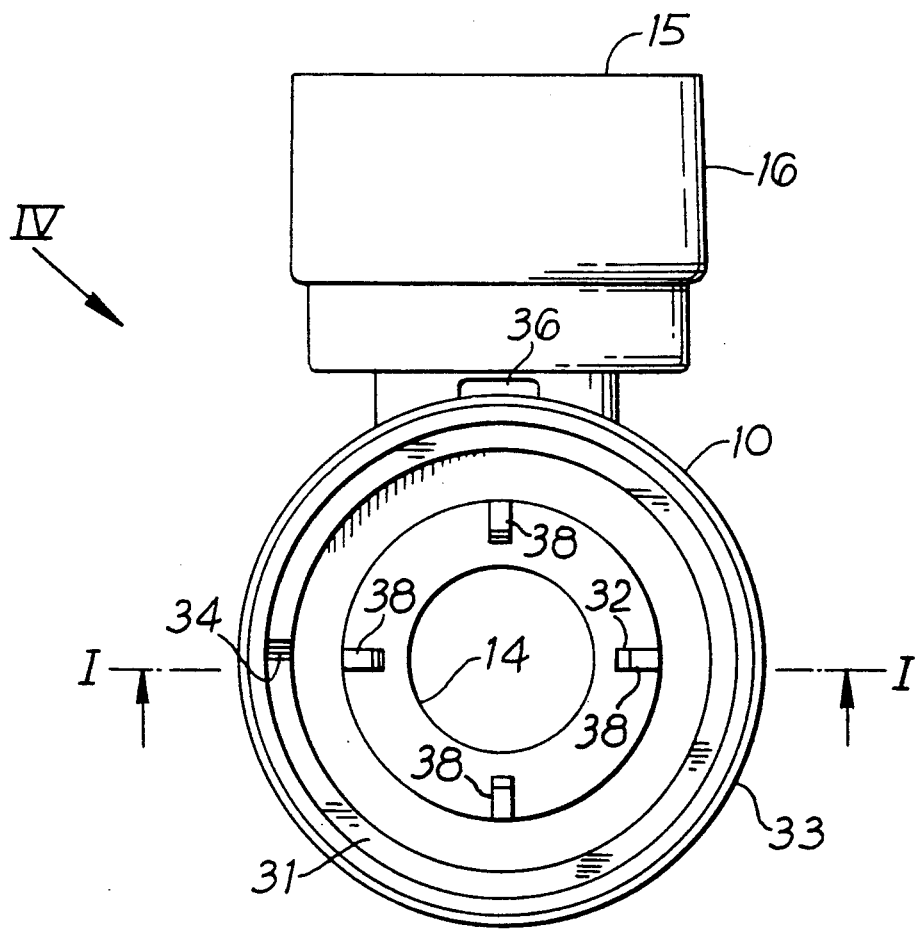
Figure 4:
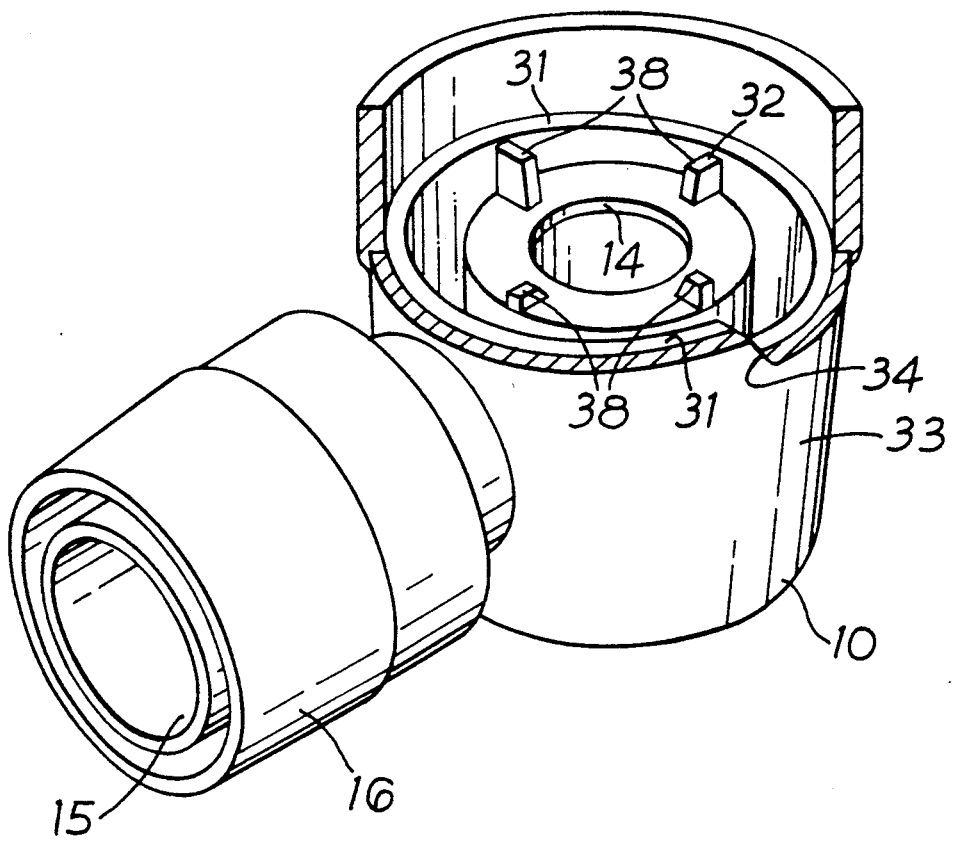

Embodiments of the invention will now be described by way of non-limitative example with reference to the accompanying Drawings, in which:

FIG. 1 is a sectional side elevation of a valve assembly in an exploded condition taken on the line I—I in FIG. 2 and in FIG. 3, FIG. 2 is an underplan view of the valve member control element of the valve of FIG. 1 taken on the line II—II of FIG. 1, FIG. 3 is a plan view of the lower part of the valve of FIG. 1 taken on the line III—III of FIG. 1, FIG. 4 is a perspective view, partly broken away, of the lower part of the valve of FIG. 1 taken in the direction of the arrow IV in FIG. 3, and FIGS. 5 and 6 illustrate the contacting ramp surfaces of alternative arrangements comprising respectively two and four pairs of helical ramps.

The valve illustrated in FIGS. 1 to 4 is designed to maintain a predetermined gas pressure, slightly above atmospheric, in a gas pathway of a respiratory system (not shown) of the kind used in anaesthesia. In a manner known per se the system is connected to an inlet port 11 of a housing part 10 of the valve. When system pressure is great enough to overcome the resistance of a relatively light compression spring 12 the head 40 of a valve member 13 is unseated from a valve seat 41 surrounding an opening 14 to allow discharge of excess air or gas from an outlet 15 of the valve. As shown this is the central element of a connector 16 whereby flexible tubing (not shown) can be connected to the discharge side of the valve to vent excess gas. As so far described the valve is conventional. The setting of the spring 12, when in compression between a valve member control element 17 of the valve and the valve seat 41 determines in response to what excess pressure in the system the valve will open. The valve thus functions to relieve undesirable excess pressure in the system while at the same time maintaining an excess pressure sufficient to preclude any reverse flow between the outlet 15 and the inlet 11. This protects the system from ingress of any contaminant from ambience.

As also known per se the axial displacement of the valve member 13 relative to its valve seat 41 is controlled by relatively rotating upper and lower parts of the valve, thereby manually to adjust the setting of the valve to generate a greater or a lower system pressure. However this is achieved without a screw-threaded connection between upper and lower parts of the valve. In accordance with the present invention the valve member control element 17 of the valve has a cylindrical periphery 22 which is a sliding and rotary fit within a tubular bore 43 of the housing 10 of the valve. The control element 17 has a central boss 19 defining a bore 44 in which a stem 45 of a valve member 13 is a sliding fit. The valve member 13 has a head 40 at the lower end of stem 45 designed to seat on valve seat 41 to close the inlet opening 14 of the valve and a compression spring 12 surrounds the stem 45 and is entrapped between the control element 17 and the head 40 of the valve member 13.

In the assembled condition of the valve a groove 20 on the inner periphery of a central boss 21 of the a cap 18 receives a longitudinal spline (not shown) on the outer periphery of the central boss 19 of the control element 17 so that the latter is non-rotatable but axially displaceable relative to the cap 18. The cap 18 has a skirt 23 which, toward its lower, free end has on its inner periphery an annular bead 24. This will snap-engage over a shoulder 37 of the tubular wall of the housing 10. This enables the cap 18 (and with it the control element 17) to be rotated relative to the housing 10 but resists relative axial movement such as to remove the cap 18 from the housing 10. (It is preferably arranged, e.g. by making the skirt 23 sufficiently resilient, that this resistance can be overcome when it is desired deliberately to remove the cap 18 but it is sufficient to prevent unintentional disassembly of the valve cap.)

Trapped between the cap 18 and control element 17 is a relatively stronger compression spring 25. This surrounds a boss 21 of the cap and acts between a seat 26 for the spring on the underside of the web 27 of the cap and the topside of the web 28 of the control element 17 where this extends between the boss 19 (received into the boss 21) and the periphery 22 of the control element. The control element 17 is thus biassed downwardly from the cap 18 so that lower surfaces 29 and 30 of the control element 17 are held in contact with upwardly presented surfaces 31 and 32 in the interior of the housing 10 whatever the angular position of the control element 17 relative to the housing 10.

The surface 31, forming a ledge on the inner periphery of the outer wall 33 of the housing 10, is in the form of a helical ramp of constant pitch beginning and ending at a substantially vertical surface or step 34. The opposed surface 29 of the control element 17 is a helical ramp of similar, constant pitch beginning and ending at a similar step 35. The effect of the arrangement so far described is as follows: As the control element 17 is rotated with the cap 18 the ramp 29 rides over the ramp 31 causing axial displacement of the control element 17 relative to the housing 10. This displacement of the control element 17 takes place within the cap 18, which remains axially stationary relative to housing 10 through engagement of the bead 24 over the shoulder 37. Movement of the control element 17 toward or away from the valve seat 41 of housing 10 varies the gap in which the valve member 13 has axial movement and thus adjusts the leakage rate from the system and accordingly the system pressure.

It will be apparent that if control element 17 is rotated more than 360° relative to housing 10 the step 35 will pass over the step 34. In practice it is desirable to prevent this and limit the permitted angular movement of the control element 17. In the illustrated embodiment this is achieved by providing a lug 36 (FIG. 3) on the outer wall of the housing 10 at a position to engage a stop (not shown) on the cap 18 to limit the permitted angular movement of the cap, and with it the control element 17, to less than 360°.

The interaction between the helical ramps 29 and 31 during rotation of the control element 17 can best be appreciated from a consideration of the outer of the two rings in FIG. 5. In a start position (FIG. 5a) the step 35 is in contact with the step 34. The control element 17 is in the lowest possible position in housing 10 and mutual contact between the ramps 29 and 31 extends substantially throughout 360°. In FIG. 5b control element 17 has been rotated 90° relative to housing 10. The steps 34 and 35 have separated 90° and the unshaded area between them represents the arc over which the ramp 31 has ceased to support the ramp 29. In FIG. 5c the unsupported arc has become 180° and in FIG. 5d 270°. FIG. 5d represents the maximum angular movement of control element 17 relative to housing 10 permitted by the lug 36 and thus the maximum displacement of control element 17 axially away from housing 10 caused by the cooperating ramps 29 and 31. The area of residual support is represented by the residual shaded area of the outer of the two rings.

In this situation there will be a strong tendency for the control element 17 to tilt, under the influence of spring 25, out of axial alignment with housing 10 and cap 18. In accordance with the present invention this is prevented by the provision of an additional pair of opposed helical ramps 30 and 38 of similar, constant pitch angularly offset 180° relative to the firstmentioned pair, i.e. the second ramp 30 on control element 17 is offset 180° from the first ramp 29 thereof and the second ramp 38 of housing 10 is offset 180° from the first ramp 31 thereof. The formation 38 is described as a "ramp" for simplicity. In fact it consists of the upper surfaces of four equally angularly spaced abutments 32 upstanding from the inward side of the inlet 11 of housing 10 around the valve seat 41. These upper surfaces of the abutments 32 all lie on a notional helical ramp equal in pitch and diameter to the ramp 30 on part 17 and thus collectively constitute an interrupted helical ramp 38. The inner ramp 38 of housing 10 is interrupted to permit the free flow of gases between the inlet 11 and the outlet 15.

The diagram of FIG. 5 assumes, for purposes of illustration, that the inner ramp 38 of housing 10 is uninterrupted. Moreover it assumes that the inner ramp 30 of control element 17 extends through 360°. In practice this is unnecessary and it is prevented by the presence of the lug 36. The ramp 30 emerges from the underside of web 28 of control element 17 at a position 40 close to the step 39 which is its "highest" point and where it terminates. However it will be perceived that the step 39 is offset approximately 180° from the step 35.

Figure 5A:
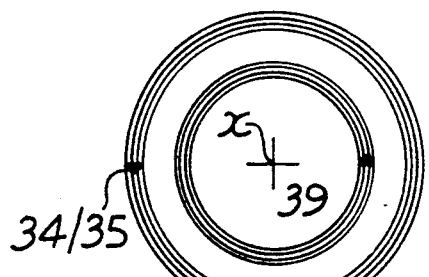
Figure 6A:
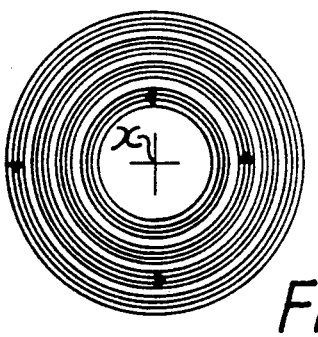
Figure 5B:
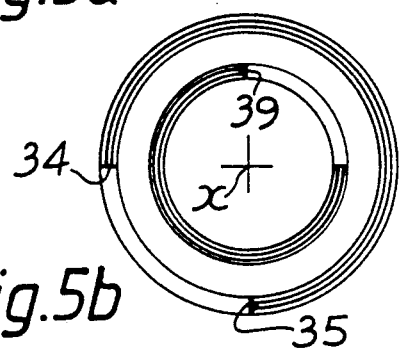
Figure 6B:
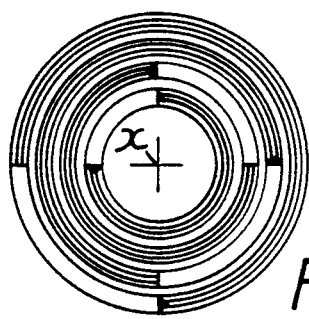
Figure 5C:
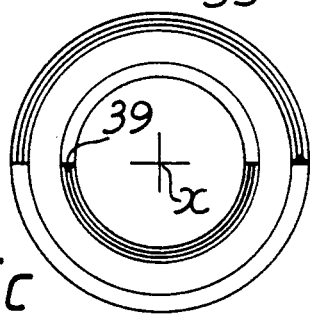
Figure 6C:
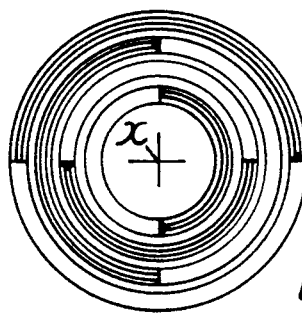
Figure 5D:
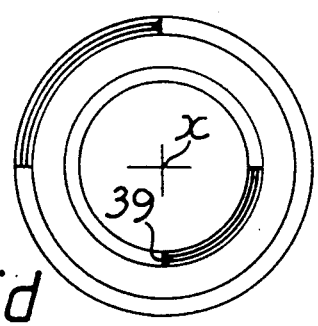
Figure 6D:
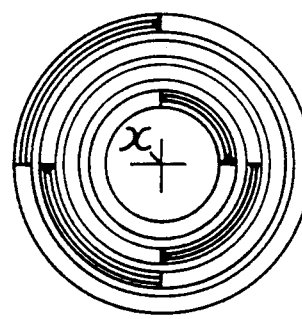
Figure 5E:
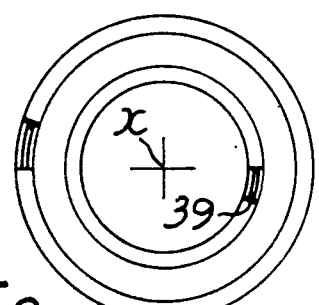
Figure 6E:
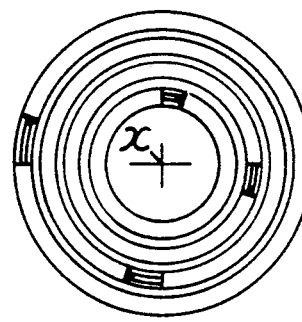

Referring again to FIG. 5, if the ramp 38 were uninterrupted the area of contact between the inner pair of ramps 30 and 38 would be as shown by the shaded part of the inner of the two rings. With control element 17 in its lowest position relative to housing 10 there will be substantially continuous contact between the inner pair of ramps when there is similar contact between the outer pair of ramps (FIG. 5a). With control element 17 rotated 90° ramp 30 moves off ramp 38 as represented by the unshaded area in FIG. 5b, and it will be noted that this is offset 180° from the unshaded area of the outer ring. Similarly in FIG. 5c where contact is lost over 180° and 5d over 270°. In FIG. 5e where contact is minimal it is to be noted that the areas of contact represented by the shaded portions of the inner and outer rings are on diametrically opposite sides of the axis x of relative rotary and axial movement of the control element 17 and housing 10.

The effect of this arrangement is that even when contact between the ramps of each pair is at a minimum (when the control element 17 is at a maximum elevation relative to the housing 10) there is still contact on opposite sides of the axis x and therefore the tendency of the upper part 17 to tilt out of axial alignment with the part 10 is resisted. It will be evident, however, that the angular offset between the two pairs of ramps need not be precisely 180° and moreover that more than two pairs of ramps may be employed. By way of example FIG. 6 illustrates an arrangement in which there are four pairs of ramps, each pair offset 90° from the or each adjacent pair. As parts bearing the respective ramps of each pair are rotated from a position of minimum (FIG. 6a) to a position of maximum (FIG. 6e) axial separation the areas of residual contact represented by the shaded portions of the four rings remain distributed around the axis x of relative rotary and axial displacement and it is particularly to be noted that in the extreme position represented by FIG. 6e residual contact is at diametrically opposite positions approximately perpendicular to one another. This provides optimum stability by preventing tilting in directions at right angles to one another.

If two pairs of ramps are employed an angular offset between them of less than 180° will provide a less stable arrangement as residual contact at maximum axial extension corresponding to FIG. 5e will not be at diametrically opposite positions. If the offset is less than 90° little advantage will be gained by the provision of two pairs of ramps because residual contact will be on the same side of the axis x. The following formula can be employed to determine the optimum angular offset between adjacent pairs of ramps:

$$\text{optimum offset} = \frac{360°}{\text{No. of concentric helical ramps.}}$$

In the embodiment of FIGS. 1–4 one of the ramps 38 of one of the pairs 30,38 is constituted by angularly spaced abutments 32. It will be appreciated that if desired one of the ramps 29 or 31 of the other pair similarly may be discontinuous. If one of the ramps of each pair is constituted by abutments such as 32 it is not essential that the remaining whole or continuous ramps should both, or all, be on the same part 10 or 17 of the valve.

A valve or tap is also envisaged in which the separate valve member 13 and associated spring 12 are dispensed with and in which the control element 17 is itself the valve member, having a surface (not shown) which will sealingly engage the valve seat 41 when approached thereto.

I claim:

1. A valve comprising a tubular housing having a valve seat therein, a valve member control element having a generally cylindrical periphery which is a sliding and rotational fit within the tubular housing, a cap covering the end of the tubular housing remote from the valve seat, said cap engaging the housing so as to be manually rotatable but not axially displaceable relative thereto and means being provided interengaging the cap and the control element whereby the control element is axially displaceable but non-rotatable relative to the cap, the housing and the control element being provided with a plurality of concentric pairs of opposed helical ramp means of different diameters, the ramp means of each pair being of similar diameter and opposed to one another axially of the housing and oppositely arranged whereby sliding contact between the ramp means as the control element is rotated will cause axial displacement of the latter toward or away from the valve seat, adjacent pairs being angularly offset about the axis of the housing. a compression spring means being entrapped between the cap and the control element to bias the latter toward the valve seat and the two ramp means of each pair being of similar, constant pitch and being configured to provide sliding contact between continuous surfaces, or between a continuous and a discontinuous surface of the ramp means of each pair when the control element and housing are relatively rotated.

2. A valve as claimed in claim 1, wherein said pairs are two in number and are angularly offset 180°.

3. A valve as claimed in claim 1, wherein opposed faces of the housing and of the control element are provided each with more than two helical ramp means of differing diameter, each said ramp means of one component being paired with a similar ramp means of the other component and each pair of ramp means being angularly offset with respect to the or each adjacent pair according to the formula:

$$\text{optimum offset} = \frac{360°}{\text{No. of concentric helical ramps.}}$$

4. A valve as claimed in claim 1 wherein the control element has an axial bore in which a stem of a valve member is axially slidable, the valve member having a head at one end of the stem between which head and the control element a compression spring is located to bias the head of the valve member into contact with the valve seat, the arrangement being such that axial displacement of the control element within the housing adjusts the pressure of the spring loading under which the head of the valve member is held on the valve seat.

5. A valve as claimed in claim 1, wherein any one of said ramp means of each pair thereof is discontinuous, being constituted by angularly separated abutments the surfaces of which presented to the other ramp means of the pair all lie on a helix of pitch and diameter similar to those of said other ramp means.

* * * * *